United States Patent [19]

Wheeler

[11] Patent Number: 4,607,621
[45] Date of Patent: Aug. 26, 1986

[54] ENDOSCOPIC APPARATUS

[75] Inventor: Robert C. Wheeler, Skaneateles, N.Y.

[73] Assignee: Welch Allyn Inc., Skaneateles Falls, N.Y.

[21] Appl. No.: 539,947

[22] Filed: Oct. 7, 1983

[51] Int. Cl.$^4$ .............................................. A61B 1/06
[52] U.S. Cl. .................................. 128/6; 128/303.15
[58] Field of Search .................................... 128/4–8, 128/303.1, 303.13–303.17; 354/62; 174/35 R, 36

[56] References Cited

U.S. PATENT DOCUMENTS

| | | | |
|---|---|---|---|
| Re. 31,289 | 6/1983 | Moore et al. | 128/6 |
| 3,834,392 | 9/1974 | Lampman et al. | 128/4 |
| 3,895,635 | 7/1975 | Justus et al. | 128/303.13 |
| 4,051,855 | 10/1977 | Schneiderman | 128/303.14 |
| 4,114,622 | 9/1978 | Gonser | 128/303.14 |
| 4,196,734 | 4/1980 | Harris | 128/303.14 |
| 4,374,517 | 2/1983 | Hagiwara | 128/6 |
| 4,375,009 | 2/1983 | Fearnside et al. | 174/35 R |
| 4,413,278 | 11/1983 | Feinbloom | 354/62 |
| 4,519,391 | 5/1985 | Murakoshi | 128/303.15 |

Primary Examiner—Edward M. Coven
Assistant Examiner—Max F. Hinderburg
Attorney, Agent, or Firm—Burns and Wall

[57] ABSTRACT

A video equipped endoscope having a solid state image sensor mounted in the distal end of an insertion tube that is connected to a video processor. The active diathermal lead of an electrosurgical generator also passes through the insertion tube in close proximity with the video components. To protect the video from the radio frequency diathermy signals, the image sensor and the video and service leads are both placed in a conductive shield that is electrically connected to the chassis of the video processor. The chassis is, in turn, electrically connected to the RF ground reference point on the electrosurgical generator whereby any radio frequency alternating current flowing through the stray capacitance between the active diathermal lead and the conductive sheath of the insertion tube as well as the conductive shield over the image sensor and service leads or RF current or voltage potentials induced by electrostatic or electromagnetic coupling between the active lead and these components are returned.

7 Claims, 3 Drawing Figures

ENDOSCOPIC APPARATUS

BACKGROUND OF THE INVENTION

This invention relates to a video endoscopic system having an electrosurgical capability and, in particular, to an electromagnetic electrostatic shield method that prevents high frequency current and voltage from adversely affecting the video section of the instrument.

As explained in greater detail in reissued U.S. Pat. Nos. Re. 31,289 and Re. 31,290 to Moore et al, endoscopes can now be equipped with small video cameras that are able to be passed into confined regions that have heretofore been inaccessible to this type of viewing equipment. The heart of the camera is a small solid state image sensor, sometimes referred to as a charge coupled device (CCD), that is able to record light images of a remote target and provide video signals indicative of the target information. A similar type system is also disclosed in U.S. Pat. No. 4,074,306 to Kakinuma et al.

As is well known, an endoscope, when used in medical applications, can provide the examining physician with a visual presentation of a remote target and also can be used as a means for carrying out certain diathermic procedures. A biopsy channel is usually housed within the insertion tube of the instrument. The active lead of a high frequency generator is passed into the viewing region of the instrument. In practice, the tissue to be treated is placed between an electrode carried at the distal end of the active lead and a plate placed against the skin of the patient near the treated area. A high frequency current is then passed through the electrode to either heat coagulate and/or cut the tissue under treatment.

When a current is passed through the human body, it will affect the myocardium by stimulating the heart muscles. Low frequency current passing through the heart muscle can cause ventricular fibrillation which oftentimes leads to death. Frequencies above 300 kHz, however, are found to have little affect on the myocardium and radio frequency currents are therefore universally used in electrosurgery of this nature. High frequency signals, however, can leak via distributed capacitance and electromagnetic and electrostatic coupling to other parts of the instrument and therefore pose a danger to both the patient and the examining physician. Precautions must be taken to prevent such leakage to exposed surfaces of the instrument that might come in contact with either person.

With the advent of video equipped endoscopes, high frequency electrosurgical generators have also been found to adversely affect the operation of the video section of the instrument. Radio frequency alternating current will flow through the stray capacitance between the active lead of the electrosurgery generator and the video and other service leads passing along the insertion tube as well as the image sensor assembly itself. High frequency alternating current will also be induced into these leads and assemblies by the electromagnetic and electrostatic fields generated by the high frequency electrosurgery current and voltage.

SUMMARY OF THE INVENTION

It is therefore an object of the present invention to improve video endoscopic systems.

A further object of the present invention is to provide a video equipped endoscope with a safe and efficient electrosurgical capability that will not disturb the video picture.

A still further object of the present invention is to shield the video sections of an endoscope from the high frequency signal of an electrosurgical device utilized in the instrument.

Another object of the present invention is to connect both the high frequency electrosurgical section and the video section of an endoscopic system to a common RF ground potential return by means of a low impedance return path.

These and other objects of the present invention are attained by means of an endoscope having a solid state image sensor mounted in the distal end of an insertion tube and video and service leads passing through the tube to a video processor, an electrosurgical generator having an active diathermic lead passing through the tube into the target region of the image sensor, a conductive shield enclosing the video signal lead that is connected to a video signal ground reference at the proximal end and the image sensor ground reference at the distal end, and an overall conductive shield enclosing both the image sensor and the video and service leads that are connected to the chassis of the video processor, and a low impedance connection for electrically joining the video processor chassis to the electrosurgical generator common radio frequency ground potential return.

BRIEF DESCRIPTION OF THE DRAWINGS

For a better understanding of these and other objects of the present invention, reference is had to the following detailed description thereof which is to be read in conjunction with the accompanying drawings, wherein.

DESCRIPTION OF THE INVENTION

Figure 1:
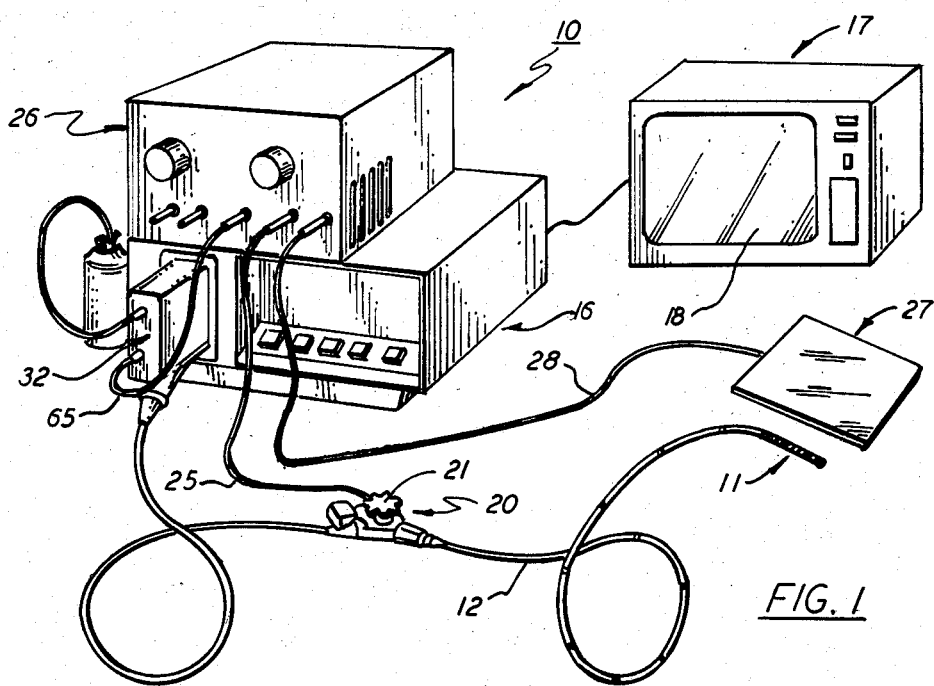
FIG. 1 is a perspective view of a video equipped endoscope having an electrosurgical generator connected thereto.
Figure 2:
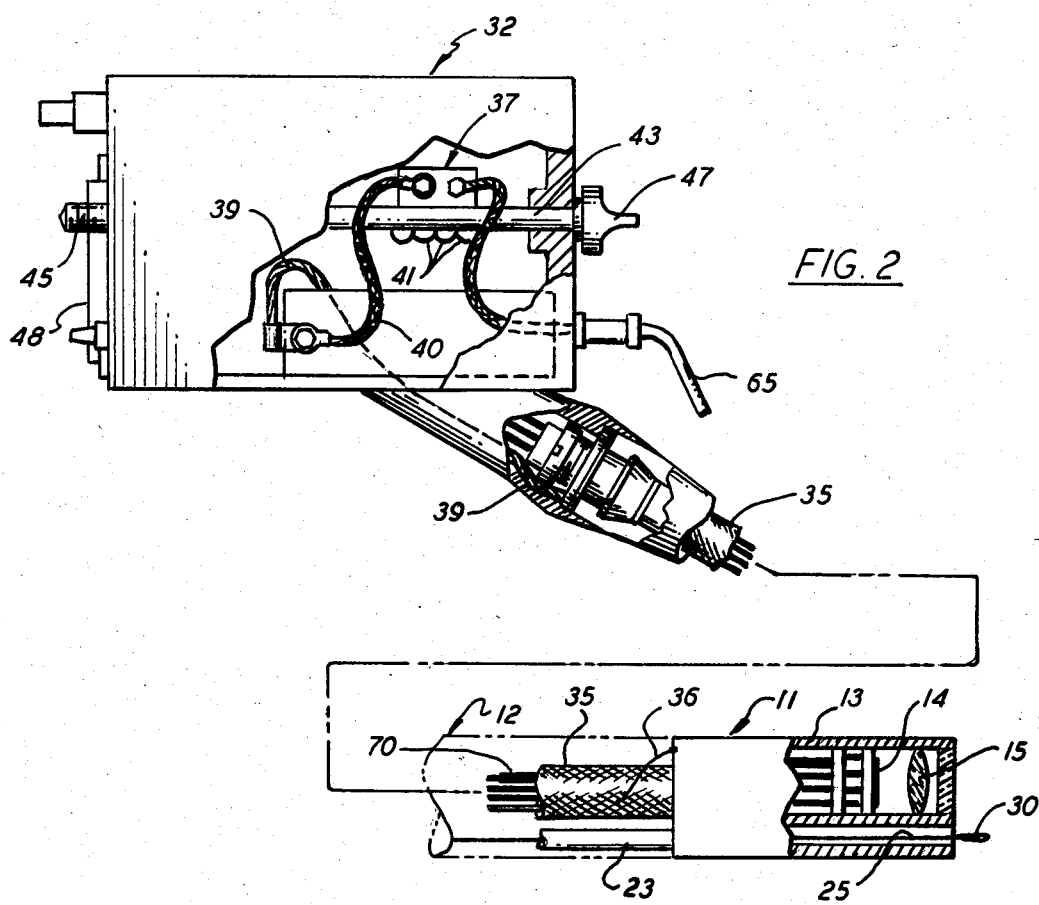
FIG. 2 is a view of the insertion tube utilized in the endoscope of FIG. 1 with portions broken away to show various internal portions thereof.

Turning now to the drawings, and, in particular, to FIG. 1, there is shown an endoscopic unit suitable for use in medical applications, generally referenced 10, that includes a video system for providing a picture of a remote target situated in the image plane of the instrument. A viewing head 11 is mounted at the distal end of the instrument's insertion tube 12. The head includes a conductive metal cylinder 13 (FIG. 2) in which is housed a solid state imager, such as a CCD image sensor 14, that is adapted to view a target in the image region of the sensor and record an image thereof. The image is focused on the recording surface of the sensor by means of lens 15.

Recorded image data is clocked out of the sensor in the form of a video signal which is transmitted by an appropriate shielded coaxial lead through the insertion tube to a video processor 16. As explained in greater detail in the Moore et al patents, light generated by a lamp or lamps situated in the processor, is carried by a fiber bundle to the viewing head for illuminating the target region and thus creating a light image of the target capable of being picked up by the image sensor. The video signals fed to the processor are placed in a desired format that is compatible with a television unit 17 so that a picture of the target is presented upon the screen 18 thereof. As can be seen, the use of the small video camera provides the attending physician with an extremely accurate picture of a desired target which typically is located in a generally inaccessible body cavity.

The nature of the video picture provided by the CCD equipped camera makes the present endoscope ideally suited for use by the physician as both a diagnostic tool and an electrosurgical instrument for carrying out certain diathermic procedures. The large screen presentation of the target enables the physician to accurately place the electrode end of an active diathermic lead directly upon the target with minimal maneuvering of the insertion tube. This greatly reduces the time that the tube remains in the body and alleviates to a large extent patient discomfort.

As shown in FIG. 1, the insertion tube of the instrument contains a steering section 20 equipped with conventional control knobs depicted at 21 that can be manipulated in a well known manner to steer the viewing head. Accordingly, the head can be maneuvered within the cavity to place the image sensor on a desired target. A biopsy channel 23 (FIG. 2) passes between the viewing head and the steering section of the instrument through which the active lead 25 of an electrosurgical generator 26 may be passed directly into the image or target region of the image sensor. The electrosurgical generator further includes a patient plate 27 that is operatively connected to the generator by a return line 28. An electrode, such as loop 30, is located at the distal end of the active lead which concentrates high frequency energy from the generator in a localized area to be treated. Electrosurgical generators of the type herein described are commercially available through Valley Laboratory, Inc., of Boulder, Colorado.

The proximal end of the insertion tube 11 is connected to a plug-in module 32 that is uniquely mated to the video processor so that the insertion tube unit can be quickly disconnected from the processor and a new unit installed between examinations. This enables the insertion tubes to be cleaned and sterilized without having to take the video processor or the electrosurgical generator out of service. The video signal lead 70 is a shielded coaxial lead connected to the video signal ground reference at the proximal end and the image sensor ground reference at the distal end. The shielded video and service leads running between the image sensor and the processor are enclosed within a conductive overall shield 35 that runs substantially the entire length of the insertion tube. The shield is typically formed of a metal braid having at least one braid wire 36 electrically connected to a conductive image sensor housing. Accordingly, both the sensor and the video and service leads are housed within a single elongated unit inside the insertion tube. The proximal end of the braided shield is electrically joined to a wiper arm assembly 37 mounted in the plug-in module by means of low impedance connectors 39 and 40. The wiper arm assembly contains a series of spring-like fingers 41—41 that ride in biasing contact against the shank of pull-in bolt 43. The threaded end 45 of the bolt is received within the chassis of the video processor and when turned via finger engageable knob 47 draws the module tightly into the processor receiving slot. As can be seen through use of the wiper arm and bolt arrangement the overall shield and the image sensor housing are both electrically connected to the processor chassis. The remaining video and service leads passing through the overall shield are wired through their associated circuitry into a male plug 48 that fits into a complementary female socket contained in the video processor.

Figure 3:
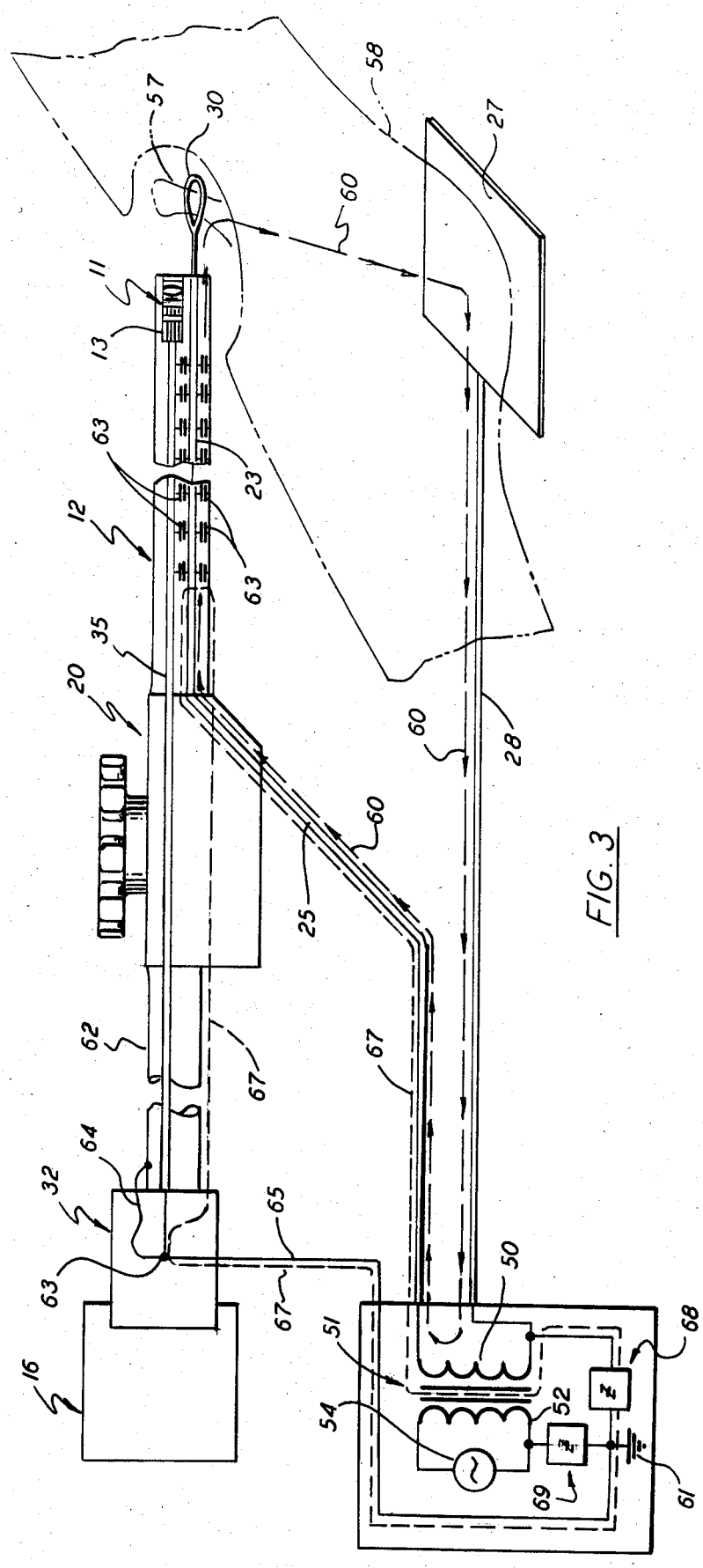
FIG. 3 is a diagrammatic presentation of the diathermy system used in the present endoscope showing the low impedance circuit for returning high frequency current that might leak from the normal electrosurgical path back to the system ground.

Turning now more specifically to FIG. 3, there is shown schematically both the video system and the diathermy system of the present endoscope. The active and patient plate leads of the diathermy section are connected to the secondary winding 50 of a radio frequency (R.F.) generator 51. The secondary winding is returned through a discrete or stray impedance 68 to an R.F. ground reference 61. The primary winding 52 of the generator is connected to suitable oscillator 54 and both are returned through an impedance 69 to an RF ground reference 61. The electrode end of the active lead includes a loop 30 that is shown encircling a polyp 57 that is undergoing diathermic treatment. The patient's body 58, shown in phantom outline rests upon the patient plate 27 and provides a means for allowing current to flow from the electrode to the plate. The plate closes the current path back to the generator via lead 28. The path of current for the radio frequency is shown in FIG. 3 by the arrows 60—60.

The insertion tube of the present endoscope is enclosed within a cylindrical outer casing that includes a flexible conductive metal sheath 62 which provides both body and strength to the unit so that it can be pushed along by the physician and yet still be maneuvered by use of the steering section. As shown in FIG. 3, the metal sheath of the insertion tube is connected to the wiper arm assembly at point 63 by means of a low impedance line 64. The wiper arm assembly, in turn, can be connected directly to the R.F. ground reference 61 by means of a cord 65 that passes from the plug in module unit 32 to the high frequency generator as shown in FIG. 1. As can be seen, through use of the present arrangement, the insertion tube sheath, the video and service wire shield, the image sensor housing and the chassis of the video processor are all brought to the same common ground, and are therefore held at the same RF voltage potential. Any radio frequency current that might be coupled or induced into any of these surfaces is provided with a low impedance return path to the original R.F. source. Concurrently any radio frequency signals that would otherwise be coupled through stray capacitance or electromagnetic and electrostic coupling into the image sensor assembly or video and service leads are, instead, intercepted or blocked by the described shielding method. The induced and coupled RF current is returned to the RF source ground reference by the described shield return method, and the induced and coupled RF voltage is reduced to a very low level by the described low impedance common "grounding" method. This low impedance path is depicted schematically by the dotted lines 67 in FIG. 3. Furthermore, by providing this low impedance common grounding and shielding method, the various shields and chassis surfaces are held at a substantially common RF potential thereby reducing R.F. signal coupling into nearby circuitry. The video and service signals are effectively shielded from the adverse effects of stray capacative, electromagnetic and electrostatic coupling which would otherwise adversely affect the operation of the video section.

While this invention has been described with specific reference to the embodiment herein disclosed, it should be evident that the present invention is broad enough to cover any modifications or changes as may come within the scope of the following claims.

I claim:

1. A video-equipped endoscope for performing diathermic treatment in the viewing region of the instrument, said endoscope having an image sensor mounted in the distal end of an insertion tube that is connected to a remote video processor by video lead means passing through the insertion tube, and a diathermic lead also passing through the insertion tube that is connected to a high frequency R.F. electro-surgical generator, the improvement comprising video ground means for placing video related components at a video ground reference potential, R.F. ground means for placig the electro-surgical generator at an R.F. ground reference potential, a conductive shield mounted inside the insertion tube for enclosing the video image sensor and the video lead means, first means for connecting the shield to the video ground means, and second means for connecting the shiled to the R.F. ground means whereby electrical energy coupled to the shield is returned to the appropriate ground reference.

2. The improvement of claim 1 that further includes a conductive sheath enclosing the insertion tube and further means to connect the sheath to the video ground means and to the R.F. ground means.

3. The improvement of claim 1 that further includes a patient plate for contacting the body of a patient undergoing diathermic treatment and means to connect the plate to the R.F. ground means.

4. In a video-equipped endoscope having an image sensor mounted in the distal end of an insertion tube that is operatively connected to a remote video processor by video lead means passing through the tube, and a diathermic lead passing through the tube that is connected to an R.F. electro-surgical generator, the improvement comprising grounding means for connecting the chassis of the video processor at a video ground reference potential and an R.F. ground reference potential, a plug-in connector for removably connecting the insertion tube to the video processor, said connector having a conductive member that is threadably mated to the chassis of the processor, a conductive shield mounted inside the insertion tube for enclosing the image sensor and the video lead means, a conductive sheath enclosed the insertion tube whereby the diathermic lead is positioned between the conductive shield and the conductive sheath, a contact means that is in contact with the threaded member, a first grounding lead for electrically coupling the sheath to said threaded member, and a second grounding lead for electrically coupling the shield to said contact whereby both the sheath and the shield are grounded to the chassis when the insertion tube is connected to the processor.

5. The improvement of claim 4 wherein said threaded member is a manually operated bolt rotatably supported in the connector that is received within a threaded hole formed in the chassis.

6. The improvement of claim 5 wherein said contact means is a spring-biased finger that rides in moving contact against the bolt member.

7. The improvement of claim 6 that further includes a patient plate for contacting the body of a patient undergoing diathermic treatment and means to connect the plate to the R.F. ground reference potential.

* * * * *

UNITED STATES PATENT AND TRADEMARK OFFICE
CERTIFICATE OF CORRECTION

PATENT NO. : 4,607,621

DATED : August 26, 1986

INVENTOR(S) : ROBERT C. WHEELER

It is certified that error appears in the above-identified patent and that said Letters Patent is hereby corrected as shown below:

Column 5, line 18 - "placig" should read --placing--; and line 25 - "shiled" should read --shield--.

Signed and Sealed this

Twenty-fourth Day of March, 1987

Attest:

DONALD J. QUIGG

Attesting Officer — Commissioner of Patents and Trademarks